(12) United States Patent
Guillaume et al.

(10) Patent No.: US 7,470,809 B2
(45) Date of Patent: Dec. 30, 2008

(54) PROCESS FOR THE PRODUCTION OF [2-(4-FLUORO-BENZYL)-PHENYL]-ACETIC ACID

(75) Inventors: Michel Joseph Maurice André Guillaume, Berg (BE); Yolande Lydia Lang, Vosselaar (BE); Armin Roessler, Tengen (CH); Lars Ulmer, Neuhausen (CH); Stefan Marcel Herman Leurs, Vosselaar (BE); Dirk De Smaele, Wetteren (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/574,300

(22) PCT Filed: Aug. 26, 2005

(86) PCT No.: PCT/EP2005/054202

§ 371 (c)(1),
(2), (4) Date: Feb. 26, 2007

(87) PCT Pub. No.: WO2006/024630

PCT Pub. Date: Mar. 9, 2006

(65) Prior Publication Data

US 2007/0213556 A1  Sep. 13, 2007

(30) Foreign Application Priority Data

Aug. 31, 2004 (WO) ............... PCT/EP2004/051969

(51) Int. Cl.
C07C 51/00 (2006.01)
C07C 55/28 (2006.01)

(52) U.S. Cl. ........................ 562/406; 562/489
(58) Field of Classification Search ........................ None
See application file for complete search history.

(56) References Cited

U.S. PATENT DOCUMENTS 6,998,494 B2* 2/2006 Lang et al. .................. 549/457

7,205,335 B2* 4/2007 Hua et al. ................... 514/468
2002/0062041 A1* 5/2002 Geissler ...................... 562/495
2002/0062401 A1* 5/2002 Auslander et al. ........... 709/312

FOREIGN PATENT DOCUMENTS

| CN | 1690042 A | * | 2/2005 |
| WO | WO 03/048146 A1 | | 6/2003 |
| WO | WO 03/048147 A2 | | 6/2003 |

OTHER PUBLICATIONS

Hahn Tetrahedron 46(1924) 1645-53.*
International Search Report (PCT/EP2005/054202) PRD2295f dated Jan. 16, 2006.

* cited by examiner

Primary Examiner—Daniel M Sullivan
Assistant Examiner—Louisa Lao

(57) ABSTRACT

The present invention relates to a novel process for the production of [2-(4-fluoro-benzyl)-phenyl]-acetic acid, a compound obtainable from phthalic anhydride. The process comprises the subsequent steps a) through e):

a) reacting phthalic anhydride with fluorobenzene or a derivative thereof in appropriate reaction conditions;
b) over reducing the product obtained in step a) at the ketone moiety;
c) reducing the product obtained in step b) with sodium dihydro-bis(2-methoxyethoxy)aluminate (Red-Al) to the corresponding alcohol;
d) chlorinating the alcohol obtained in step c);
e) inserting CO into the product obtained in step d) through an appropriate Pd-containing catalytic system.

In an alternative embodiment, the step e) is replaced by the steps f1) and f2):
f1) reacting the product obtained in step d) with sodium cyanide;
f2) hydrolysing the product obtained in step f1).

The present invention provides a process for the production of [2-(4-fluoro-benzyl)-phenyl]-acetic acid which is suitable for industrial scale reactors (e.g. which is cleaner and more efficient). Also, [2-(4-fluoro-benzyl)-phenyl]-acetic acid is obtained as a crystalline material with a purity >95%.

9 Claims, No Drawings

PROCESS FOR THE PRODUCTION OF [2-(4-FLUORO-BENZYL)-PHENYL]-ACETIC ACID

CROSS REFERENCE TO RELATED APPLICATIONS

This application is the national stage of Application No. PCT/EP2005/054202, filed 26 Aug. 2005, which application claims priority from PCT/EP2004/05 1969 filed 31 Aug. 2004.

The present invention relates to a novel process for the production of [2-(4-fluoro-benzyl)-phenyl]-acetic acid, a compound obtainable from phthalic anhydride.

This derivative is an important intermediate in the synthesis of a series of compounds, disclosed in WO 97/38991, having the general formula (A) wherein $R^1$ and $R^1$ are inter alia hydrogen and/or methyl, $R^3$ and $R^4$ are hydrogen or halogen, X is $CH_2$, O or S, n is 1 and p and q are 0, 1 or 2.

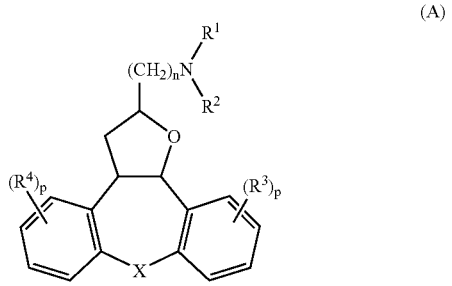

Compounds according to Formula (A) were found useful for the treatment and/or the prevention of CNS disorders, cardiovascular disorders and gastrointestinal disorders. Their synthesis has, among others, been described in WO03/048146 and WO03/048147. In the latter documents (see Scheme 1), it has been disclosed that the [2-(4-fluoro-benzyl)-phenyl]-acetic acid according to Formula (I) can be prepared by adaptation of an art-known sequence (French Patent. No. 4395M, dated Oct. 10, 1966; Can. J. Chem., 1971, 49, 746-754) starting with a Friedel-Crafts acylation reaction using fluorobenzene and phthalic anhydride to form a keto-acid according to Formula (IV), followed by reductive removal of the ketone group and homologation of the carboxylic acid function.

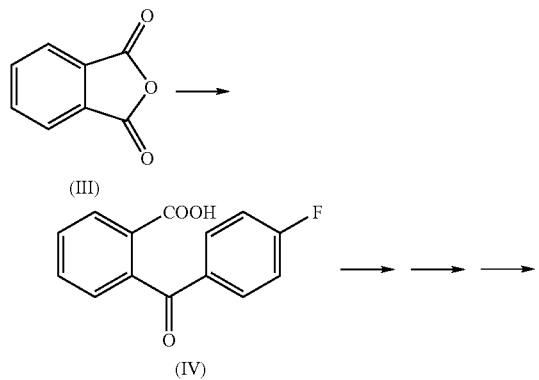

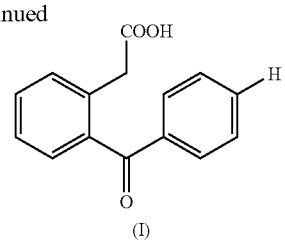

The problem with this reaction scheme is that several steps of the synthesis suffer from diverse drawbacks: environmentally unfriendly solvents, low yield, use of complex reagents or formation of undesired salt mixtures, such as, for example $Et_3NH^+Cl^-$.

The object of the present invention is to provide a process for the production of [2-(4-fluoro-benzyl)-phenyl]-acetic acid which is suitable for industrial scale reactors (e.g. which is cleaner and more efficient).

A further object of the present invention is to provide a process such that [2-(4-fluoro-benzyl)-phenyl]-acetic acid is obtained as a crystalline material with a purity >95%.

Very surprisingly, the inventors have found that the drawbacks of the known processes can be overcome by a process which comprises the subsequent steps a) through e).

a) reacting phthalic anhydride with fluorobenzene or a derivative thereof in appropriate reaction conditions;

b) over reducing the product obtained in step a) at the ketone moiety;

c) reducing the product obtained in step b) with sodium dihydro-bis(2-methoxyethoxy)aluminate (Red-Al) to the corresponding alcohol;

d) chlorinating the alcohol obtained in step c);

e) inserting CO into the product obtained in step d) with the use of an appropriate catalytic system.

A similar reaction step e) per se is disclosed in EP 1 207 148 A1 (Clariant GmbH, 22 May 2002).

The process according to the invention can schematically be depicted as follows (see Scheme 2):

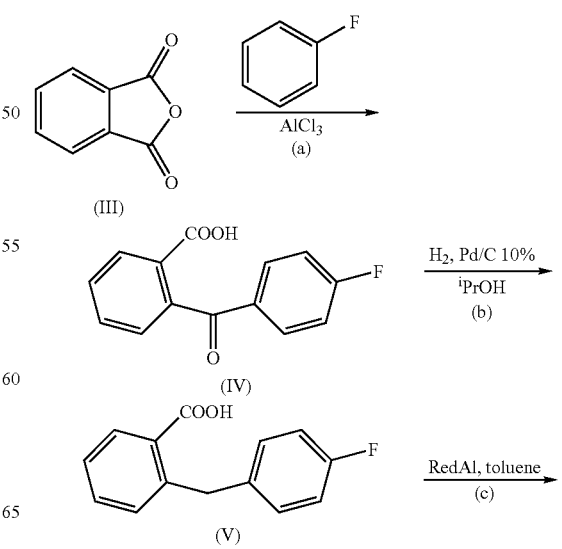

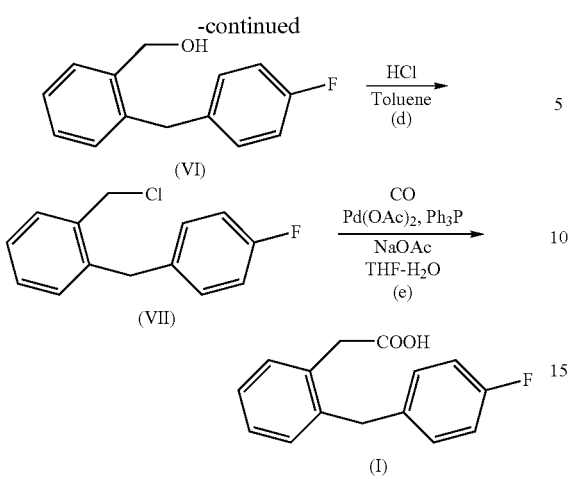

Preferentially, in step a), a Friedel Crafts reaction is used using fluorobenzene itself as solvent and aluminium chloride as the Lewis acid for the Friedel-Crafts reaction. Preferably, aluminium chloride is used in a molar ratio related to phthalic anhydride >2:1. Using less aluminium chloride leads to incomplete conversion. Preferentially, in step a), the reaction is performed at reflux temperature of fluorobenzene, which is about 75-80° C. When the reaction is performed at a lower temperature, the reaction rate decreases. Preferentially, the reaction mixture obtained in step a), which includes a number of aluminium salts, is hydrolysed with aqueous hydrochloric acid.

Preferentially, in step b), the reaction is performed using hydrogen gas, optionally in the presence of a Pd/C catalyst and using isopropanol (iPrOH) as solvent. Using methanol (MeOH) instead leads to decreased reaction rate. Using water leads to formation of impurities. Preferentially, in step b), the reaction is performed at a temperature above 45° C. Below 45° C., the reaction is too slow.

Preferentially, in step c), 2.3 equivalents of sodium dihydro-bis(2-methoxyethoxy)aluminate ("RedAl") is used. Using less reducing agent could lead to a lower conversion. Preferentially, in step c), toluene is used as a solvent. Toluene is the solvent in which the commercial sodium dihydro-bis (2-methoxyethoxy)aluminate ("RedAl") is dissolved. Due to the reactive nature of this reductant, it is not possible to use protic solvents. Moreover, it is not necessary to isolate the product obtained in step (c) after work-up because the toluene solution comprising the product is used as it is.

Preferentially, in step d) aqueous hydrochloric acid is used as the chlorinating agent. Preferentially, in step d), the reaction is performed at 90° C. The reaction rate is lower at a lower temperature. Preferentially, in step d), the reaction is performed in a closed vessel (pressure build-up occurs to about 1.5 atmosphere). In an open vessel, hydrochloric acid partially evolves.

Preferentially, in step e), the product obtained from step d) is reacted with CO in a mixture of THF and H₂O, preferably in a 1:1 ratio, using a Pd-containing catalytic system. Water is necessary to bring about the hydrolysis of the intermediate palladium complex. Its combination with THF gives the highest conversion. As a catalytic system for this reaction step, preferably sodium acetate is used. If sodium acetate is omitted, hardly any reaction takes place. Other systems comprise potassium carbonate or triethylamine. Preferentially, in step e), the reaction is performed using triphenylphosphine (Ph₃P) as a ligand for palladium. Other ligands have been tested, but results are not better. Ph₃P is the more common one and is preferentially used. Preferentially, in step e), the reaction is performed at a pressure of 4 bars. At atmospheric pressure, the reaction is very slow. Preferentially, in step e), the reaction is performed at a temperature of 80° C. At a lower temperature, the reaction is slower.

According to another embodiment related to the invention the process comprises the subsequent step a) through f2), differing from the previous described process in that step e) has been replaced by steps f1) and f2):

a) reacting phthalic anhydride with fluorobenzene using fluorobenzene itself as solvent and aluminium chloride as the Lewis acid for the Friedel-Crafts reaction at reflux temperature;

b) over reducing the product obtained in step a) at the ketone moiety;

c) reducing the product obtained in step b) with sodium dihydro-bis(2-methoxyethoxy)aluminate (Red-Al) to the corresponding alcohol;

d) chlorinating the alcohol obtained in step c);

f1) reacting the product obtained in step d) with sodium cyanide;

f2) hydrolysing the product obtained in step f1).

The process according to the invention can be depicted as follows (see Scheme 3):

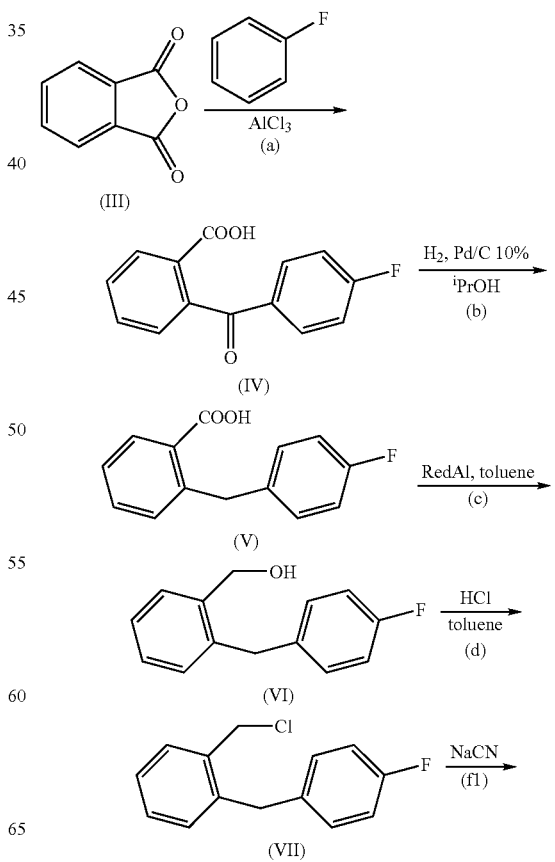

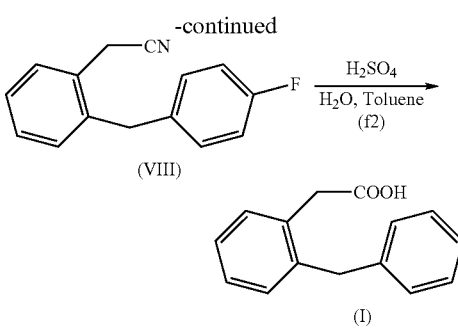

For steps a) through d) the preferential embodiments have been described above.

Preferentially, in step f1), the reaction is performed at 70° C. in a mixture toluene/water in presence of a phase-transfer catalyst (such as tetrabutylammonium hydrogenosulfate (TBAHS)). Preferentially, in step f1), the reaction is performed in a mixture of acetic acid, sulphuric acid and water at reflux.

The processes according to the invention will now be elucidated using the following examples, without being limited thereto.

Experimental

All materials were purchased from commercial suppliers and used without further purification. Reactions were conducted under an atmosphere of nitrogen, when necessary. In the lab, only glass vessels were used; in the pilot plant, both steel or glass-lined vessels are used. For each reaction, a sample of the reaction mixture was collected and analysed by means of HPLC.

EXAMPLE

Step a) 2-(4-fluoro-benzoyl)-benzoic acid (Compound IV)

1. A solution of p-fluorobenzenemagnesium bromide (1.2 M solution in THF, 1 eq.) is added to a 0.4 M solution of phthalic anhydride in THF, so that the temperature remains under 30° C. After 1 hour, half of the solvent is distilled off and the reaction mixture is stirred overnight at room temperature. The obtained precipitate is filtered off and taken up in water (0.3 L/mol). Toluene (1 L/mol) and HCl$_{cp}$ are added so that the temperature remains under 35° C. After stirring for 1 hour, the organic layer is evaporated (50° C., vacuum) and the obtained solid is dried at 50° C. under vacuum. Active yield: 69%.

2. Alternatively, a Friedel-Crafts reaction can be performed. In an inertized flask containing phthalic anhydride, fluorobenzene (1.8 L/mol), is added, followed by cautious addition of aluminium chloride (2.1 eq.). The reaction mixture is heated up to 75° C. (HCl evolution is observed). After 3 hours at 75° C., water is added (1 L/mol). The organic layer is separated and concentrated hydrochloric acid (0.1 L/mol) is added. Fluorobenzene is distilled off and the mixture is cooled down to 10° C. The precipitate is filtered off, washed with water and dried at 65-70° C. Active yield: 85%. N.B. Fluorobenzene can be recuperated by washing with an alkaline solution and discarding the water layer.

Step b) 2-(4-fluoro-benzyl)-benzoic acid (Compound V)

In a hydrogenation flask was added 2-(4-fluoro-benzoyl)-benzoic acid, propylene glycol monomethyl ether (1 L/mol) and Pd/C 10% wet (15 g/mol). Hydrogenation was performed at 50° C. over 18 hours. Thiophene (0.3 kg/mol) was added and the catalyst was filtered off. The filtrate was heated up to 80° C. and water (1.12 L/mol) was added at that temperature. The mixture was heated up to reflux, then cooled down to 25° C. and stirred at that temperature during 1 hour. The precipitate was filtered off, washed with water (1 L/mol) and dried at 50° C. during 18 hours. Active yield: 83%.

Step c) [2-(4-fluoro-benzyl)-phenyl]-methanol (Compound VI)

In an inertized flask containing 2-(4-fluoro-benzyl)-benzoic acid (1 eq.), toluene (0.8 L/mol) is added and the vessel is cooled down to 0-5° C. Sodium dihydro-bis(2-methoxyethoxy)aluminate ("RedAl") (1 M in toluene, 2.3 eq.) is added dropwise and the reaction mixture is stirred at 5° C. during 16 hours. Acetone (3 eq.) is added dropwise at 5° C. and the mixture is stirred during 15 minutes. The temperature is allowed to rise to 25° C. A sodium hydroxide solution (5 eq.) is added and the mixture is stirred vigorously during 20 minutes. The organic layer is separated and washed again with a slightly acidic aqueous solution. The organic layer is filtered over Dicalite and used further in the next step.

Step d) [2-(4-fluoro-benzyl)-phenyl]-chloromethane (Compound VII)

In an inertized vessel containing [2-(4-fluoro-benzyl)-phenyl]-methanol solution in toluene, HCl$_{cp}$ (5 eq.) is added, the vessel is closed and the mixture is stirred to 90° C. (a pressure of 1.54 bar develops). After 6 hours at 90° C., the reaction mixture is cooled down to 25° C. and the vessel is opened. The layers are separated, the organic layer is washed with water, then with slightly alkaline solution and used further in the next step.

Step e) [2-(4-fluoro-benzyl)-phenyl]-acetic (Compound I)

[2-(4-fluoro-benzyl)-phenyl]-chloromethane (1 eq.), THF (1 L/mol), water (0.7 L/mol), Pd(OAc)$_2$ (1.3 mol %), dppp (2.6 mol %) and sodium acetate (2.5 eq.) were placed in a inertized reactor. The reaction mixture is placed under a CO pressure of 4 bars and allowed to stir at 80° C. for 20 hours. The organic layer is separated and evaporated under pressure. Toluene (0.75 L/mol) is added to the residue and the carboxylic acid is extracted with a 2 N solution of sodium hydroxide (0.75 L/mol). The black particles of palladium are removed by filtration over Celite. The water layer is placed in a flask and acetic acid (0.9 L/mol) is added. The mixture is warmed up to 80° C. then allowed to spontaneously cool down. The crystallisation starts around 50° C. The crystals are filtered off at room temperature, washed with water and dried to give black [2-(4-fluoro-benzyl)-phenyl]-acetic acid (91%). Treatment of 5 g of black [2-(4-fluoro-benzyl)-phenyl]-acetic acid with charcoal in 25 ml of a mixture of acetic acid and water (7/3) allows the isolation of pure white crystals of [2-(4- fluoro-benzyl)-phenyl]-acetic acid. This step can be performed before the first addition of acetic acid.

Step f1) [2-(4-fluoro-benzyl)-phenyl]-acetonitrile (Compound VIII)

2-(4-fluoro-benzyl)-benzoic acid is dissolved in toluene (1.5 L/mol) and DMF (1 ml/mol) is added. The reaction mixture is heated up to 40° C. and thionyl chloride (1.1 eq.) is added. During the addition the reaction mixture is further heated up to 50° C. The reaction mixture is stirred at 50° C. during 2.5 hours, then evaporated at 50° C. under vacuum. THF (0.3 L/mol) is added and that solution is dropped into a 2 M $NaBH_4$ solution in THF (1.5 eq.). The temperature rises to reflux (67° C.) and the reaction mixture is stirred at reflux during 2 hours. The reaction mixture is cooled down to room temperature. Acetone (350 ml/mol) is added (temperature rises to 40° C.), the reaction mixture is stirred during 30 minutes, followed by toluene (1 L/mol) and water (1.5 L/mol). The reaction mixture is heated up to 50° C. and the organic layer is evaporated at 50° C. under vacuum. $CH_2Cl_2$ (3 L/mol) is added, followed by triethylamine (1.1 eq.). $SOCl_2$ (1.1 eq.) is added dropwise, the temperature rises to reflux. The reaction mixture is stirred during 45 min to room temperature. Water (1 L/mol) is added and the reaction mixture is stirred vigorously during 15 min. The organic layer is washed a second time with water (1 L/mol) and evaporated (40° C., vac.). The product is dissolved in toluene (2.5 L/mol), tetrabutylammonium hydrogenosulfate (phase-transfer catalyst) (0.1 eq.) is added at 70° C. and sodium cyanide 6 M (1.6 eq.) is added at 70° C. under vigorous stirring. The reaction mixture is then heated up to reflux and stirred during 3 hours. After cooling down to room temperature, water (0.5 L/mol) is added and the reaction mixture is stirred during 30 minutes. After washing a second time with water (0.5 L/mol), drying on magnesium sulphate and evaporating the solvent, [2-(4-fluoro-benzyl)-phenyl]-acetonitrile is obtained. Active yield: 94%. N.B. The product can be purified with e.g. thin-film distillation.

Step f2) [2-(4-fluoro-benzyl)-phenyl]-acetic acid (Compound I)

[2-(4-fluoro-benzyl)-phenyl]-acetonitrile is suspended in acetic acid (0.5 L/mol), water (0.3 L/mol) and sulphuric acid (0.35 L/mol). After 5 hours at reflux, the mixture is cooled down, water (1.2 L/mol) and dichloromethane (0.3 L/mol) are added. The organic extract is washed with water (1.3 L/mol) and sodium hydroxide 50% (0.15 L/mol). After stirring for 20 min., the aqueous layer is separated and washed with $CH_2Cl_2$ (0.1 L/mol) which is discarded. The aqueous layer is acidified with concentrated hydrochloric acid (2 eq.). The mixture is stirred during 3 hours, the precipitate is then filtered off and washed with water (0.1 L/mol). Yield: 74%.

Every step has been optimised in the lab, then successfully scaled-up in the pilot plant.

The invention claimed is:
1. Process for the production of [2-(4-fluoro-benzyl)-phenyl]-acetic acid, comprising the subsequent steps a) through e):
   a) reacting phthalic anhydride with fluorobenzene or a derivative thereof in a Friedel Crafts reaction under appropriate reaction conditions to produce the compound of formula:

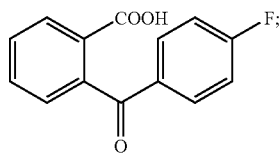

b) reducing the product obtained in step a) at the ketone moiety to produce a compound of the formula:

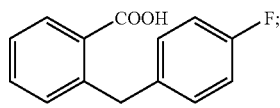

c) reducing the product obtained in step b) with sodium dihydro-bis (2-methoxyethoxy) aluminate (Red-Al) to the corresponding alcohol;
   d) chlorinating the alcohol obtained in step c);
   e) reacting the product obtained in step d) with CO utilizing an appropriate Pd-containing catalytic system to produce the compound of the formula:

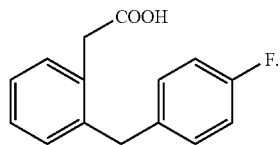

2. Process for the production of [2-(4-fluoro-benzyl)-phenyl]-acetic acid, comprising the subsequent steps a) to d) then f1) and f2):
   a) reacting phthalic anhydride with fluorobenzene or a derivative thereof in a Friedel Crafts reaction under appropriate reaction conditions to produce the compound of formula:

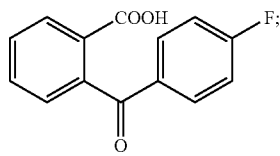

b) over reducing the product obtained in step a) at the ketone moiety to produce a compound of the formula:

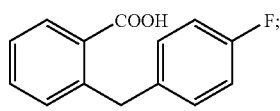

c) reducing the product obtained in step b) with sodium dihydro-bis (2-methoxyethoxy) aluminate (Red-Al) to the corresponding alcohol;
   d) chlorinating the alcohol obtained in step c);
   f1) reacting the product obtained in step d) with sodium cyanide;
   f2) hydrolysing the product obtained in step f1).

3. Process according to claim 1 wherein in step a) the Friedel Crafts reaction is used using fluorobenzene itself as solvent and aluminium chloride as the Lewis acid.

4. Process according to claim 3 wherein in step a) aluminium chloride is used in a molar ratio to phthalic anhydride >2:1.

5. Process according to claim 1 wherein in step b) the reaction is performed using hydrogen gas, optionally in the presence of a Pd/C catalyst and using isopropanol (iPrOH) as solvent.

6. Process according to claim 1 wherein in step c) 2.3 equivalents of sodium dihydro-bis (2-methoxyethoxy) aluminate is used.

7. Process according to claim 1 wherein in step d) aqueous hydrochloric acid is used as the chlorinating agent.

8. Process according to claim 1 wherein in step e) the product obtained from step d) is reacted with CO in a mixture of THF and $H_2O$ in the presence of sodium acetate and triphenylphosphine.

9. Process according to claim 2 wherein in step f1) the reaction is performed at 70° C. in a mixture toluene/water in presence of a phase-transfer catalyst.

\* \* \* \* \*